(12) United States Patent
Tseng et al.

(10) Patent No.: US 10,420,506 B2
(45) Date of Patent: Sep. 24, 2019

(54) MODULAR INTELLIGENT CLOTHING

(71) Applicants: INVENTEC APPLIANCES (PUDONG) CORPORATION, Shanghai (CN); INVENTEC APPLIANCES CORP., New Taipei (TW)

(72) Inventors: Wen-Tso Tseng, New Taipei (TW); Kuang-Chung Chou, New Taipei (TW); Shih-Feng Huang, New Taipei (TW); Yi-Hao Wang, New Taipei (TW)

(73) Assignees: INVENTEC APPLIANCES (PUDONG) CORPORATION, Shanghai (CN); INVENTEC APPLIANCES CORP., New Taipei (TW)

( * ) Notice: Subject to any disclaimer, the term of this patent is extended or adjusted under 35 U.S.C. 154(b) by 121 days.

(21) Appl. No.: 15/486,894

(22) Filed: Apr. 13, 2017

(65) Prior Publication Data
US 2018/0168506 A1   Jun. 21, 2018

(30) Foreign Application Priority Data

Dec. 19, 2016   (CN) .......................... 2016 1 1176685

(51) Int. Cl.
| | |
|---|---|
| *H05K 7/02* | (2006.01) |
| *A61B 5/00* | (2006.01) |
| *A41D 1/00* | (2018.01) |
| *H05K 1/02* | (2006.01) |

(52) U.S. Cl.
CPC ............ *A61B 5/6804* (2013.01); *A41D 1/005* (2013.01); *A61B 5/0022* (2013.01); *H05K 1/028* (2013.01)

(58) Field of Classification Search
CPC ....................................................... A61B 5/6804
USPC ........................ 361/807; 324/754.07, 754.03
See application file for complete search history.

(56) References Cited

U.S. PATENT DOCUMENTS

| | | | |
|---|---|---|---|
| 8,035,560 B1 * | 10/2011 | Glodz | .................... G08B 21/22 342/357.71 |
| 2007/0293750 A1 * | 12/2007 | Kuo | .................... A41D 13/1281 600/388 |
| 2014/0172134 A1 * | 6/2014 | Meschter | ................ G01L 1/205 700/91 |

* cited by examiner

*Primary Examiner* — Hung S. Bui
(74) *Attorney, Agent, or Firm* — Muncy, Geissler, Olds & Lowe, P.C.

(57) ABSTRACT

A modular intelligent clothing is provided, which includes a clothing body, modular main board, and a functional board, in which the modular main board is disposed at any position of the clothing body, the functional board is disposed at any position of the clothing body, and the functional board is electrically coupled with the modular main board. The electrically connection between the functional board and the modular main board utilize the metal conductor, magnetic induction, or wireless communication. Accordingly, the functional board and the modular main board are matched each other to sense the physiological signals of the user, to position of the location of user, or to perform the home care monitoring.

10 Claims, 6 Drawing Sheets

MODULAR INTELLIGENT CLOTHING

FIELD OF THE INVENTION

The present invention relates to intelligent clothing, particularly relates to a modular intelligent clothing with a modularized main board cooperated with a functional board within clothing for sensing heartbeats and step counts, and positioning for user.

BACKGROUND OF THE INVENTION

With technology development recently, detection device or wearable device of sensing function have been developed to combine with clothing to detect or record personal physiological states, such as heartbeats, step counts, blood pressure, or sleeping state, which can be used on fields of self-health management at home or preventive medicine.

However, for elder people or people who become degenerate or disable because of wound or surgery to stay at home for home health management, it is difficult and inconvenient for them to put on or take off clothing with detection device or wearable device, and the weight of detection device or wearable device often have a load for them.

Besides, detection device or wearable device is vulnerable to dropping without good attachment on clothing or damage without careful putting-on or taking-off. Furthermore, without good attachment between detection device/wearable device and clothing is not ergonomic for people and often makes user unconformable. Consequently, the purpose of intelligent clothing is not achieved because of issues aforementioned.

SUMMARY OF THE INVENTION

With respect to the issues aforementioned, a modular intelligent clothing is provided herein to modularize current functions so as to enable them be arranged in clothing anytime for flexible design and rapid production.

With respect to the issues aforementioned, a modular intelligent clothing is provided herein to have a modular main board that may be tightly attached to clothing, ergonomically wearable like typical clothing, and conformable to people without sensing its existence.

With respect to the issues aforementioned, a modular intelligent clothing is provided herein to enable user both wear clothes including a modular main board without additional loading and take off the clothes without damage on the modular main board.

With respect to the issues aforementioned, a modular intelligent clothing is provided herein to have a main board which may be modularized, developed independently and/or up-grated, and selectively arranged with different functions for user's requirement to achieve customization, convenience, and good competition.

With respect to the issues aforementioned, a modular intelligent clothing is provided herein to have a modular main board easy to be disassembled, water-proof to be washed with clothes without circuit damage or circuit short, and good lifetime.

Accordingly, a modular intelligent clothing is provided to include: a clothing body; a metal conductor, the metal conductor arranged within the clothing body to form a circuit loop therein; a modular main board disposed at any position of the clothing body and electrically connected with the metal conductor, and having a power supply module therein; and a functional board disposed at any position of the clothing body and electrically connected with the modular main board.

Accordingly, a modular intelligent clothing is provided to include: a clothing body; a modular main board, the modular main board disposed at any position of the clothing body and having a first power supply module therein; and a functional board having a second power supply module, disposed at any position of the clothing body, and wirelessly electrically connected with the modular main board.

Accordingly, a pairing system used for the modular intelligent clothing is provided to include: a clothing body; a modular main board disposed at any position of the clothing body; and a functional board disposed at any position of the clothing body and electrically connected with the modular main board, wherein a power supply module is configured to supply a power to the modular main board or the functional board.

In one embodiment, in case that the functional board is deposited within range of magnetic induction of the modular main board, the modular main board is triggered to match with the functional board in a way of magnetic induction.

In one embodiment, in case that the functional board is deposited within wireless transmission range of the modular main board, the modular main board within the clothing body matches with the functional board in wireless way.

DETAILED DESCRIPTION OF THE PREFERRED EMBODIMENT

Figure 1:
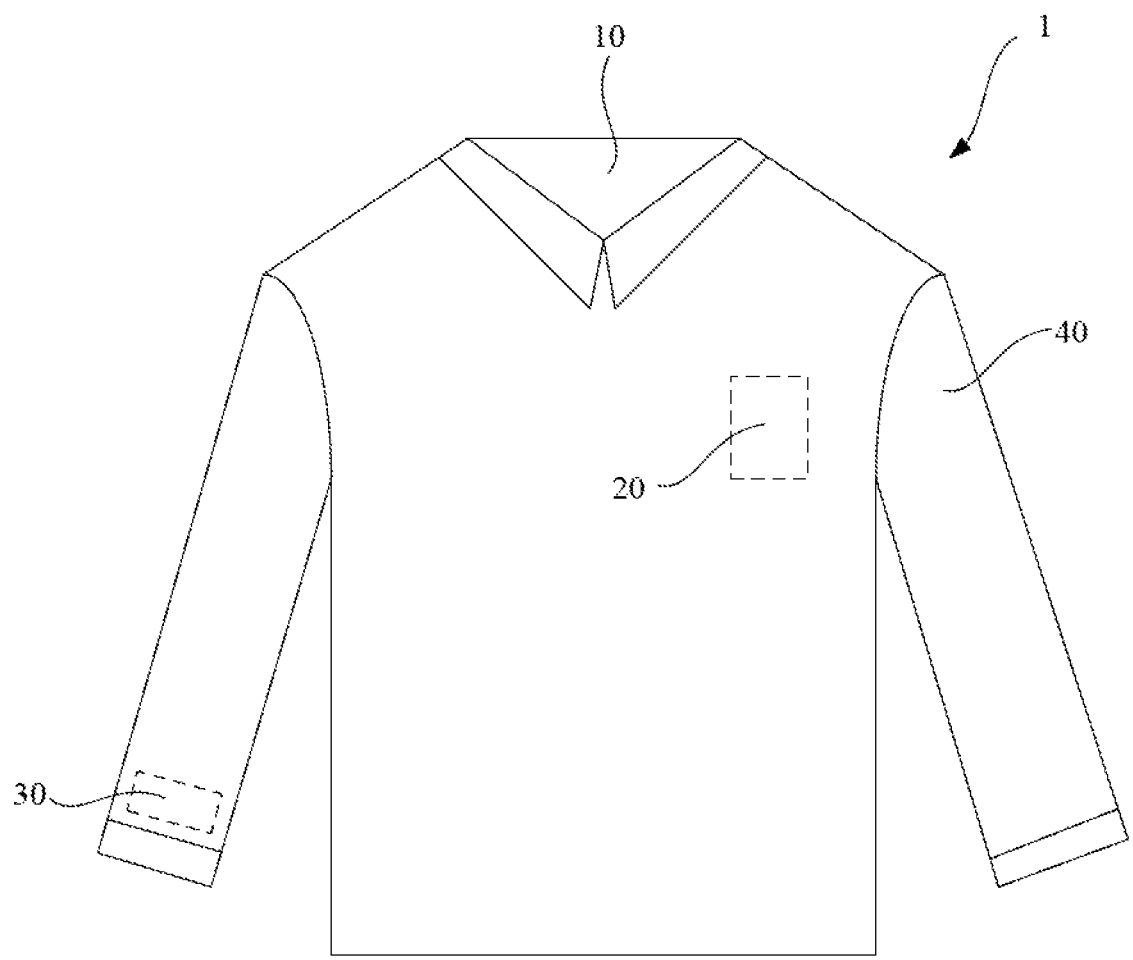
FIG. 1 is a schematic block diagram illustrating a modular intelligent clothing according to the present invention.

FIG. 1 is a schematic block diagram illustrating a modular intelligent clothing according to the present invention. Please refer to FIG. 1, a modular intelligent clothing 1 includes a clothing body 10, a modular main board 20 and a functional board 30. The modular main board 20 and the functional board 30, which are electrically connected with each other, may be arranged at any position of the clothing body 10. The electrical connection ways for the modular main board 20 and the functional board 30, for example, may be implemented with a metal conductor 40 distributed within the clothing body 10 or by magnetic induction.

Figure 2:
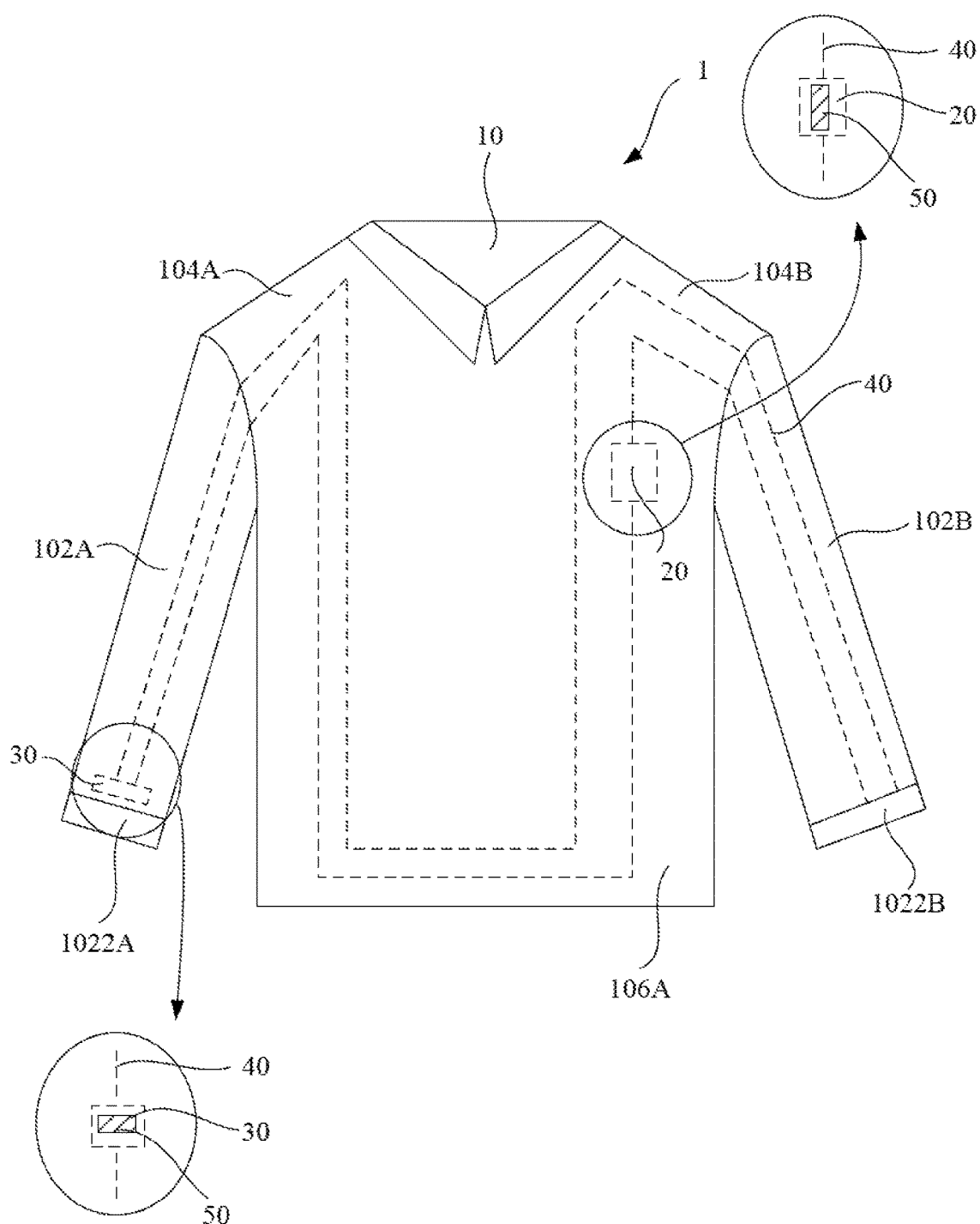
FIG. 2 is a schematic perspective diagram illustrating a clothing body with metal conductor according to the present invention.

FIG. 2 is a schematic perspective diagram illustrating a clothing body with metal conductor according to the present invention. Please refer to FIG. 2, the clothing body 10 is a coat, the metal conductor 40 is distributed within the clothing body 10 to form a circuit loop. In detail, for example, the circuit loop with the metal conductor 40 starts from a left sleeve opening 1022A to a left sleeve 102A, a left shoulder 104A, a front piece 106A, a right shoulder 104B, a right sleeve 102B, a right sleeve opening 1022B and a back piece 106B (not shown in FIG. 2) and then back to the left sleeve opening 1022A. In an embodiment, the layout of the circuit loop with the metal conductor 40 is not restricted to any starting location within the clothing body 10, and it is just completely deposited within the interior space enclosed by the clothing body 10 and constituted an electrical circuit loop.

Furthermore, the metal conductor 40 within the interior space enclosed by the clothing body 10 may consist of one or more metal wires. The metal conductor 40 is distributed in a spiral way within the clothing body 10. Besides, in consideration of convenience on user's putting on and taking off clothes and ergonomic requirement, the metal conductor 40 may be made of soft metal conductive wires. The soft metal conductive wires can be bent along with the bending of the clothing body 10 without fracturing and sway along with the swinging of the use's body, such as movement or walking.

Figure 3:
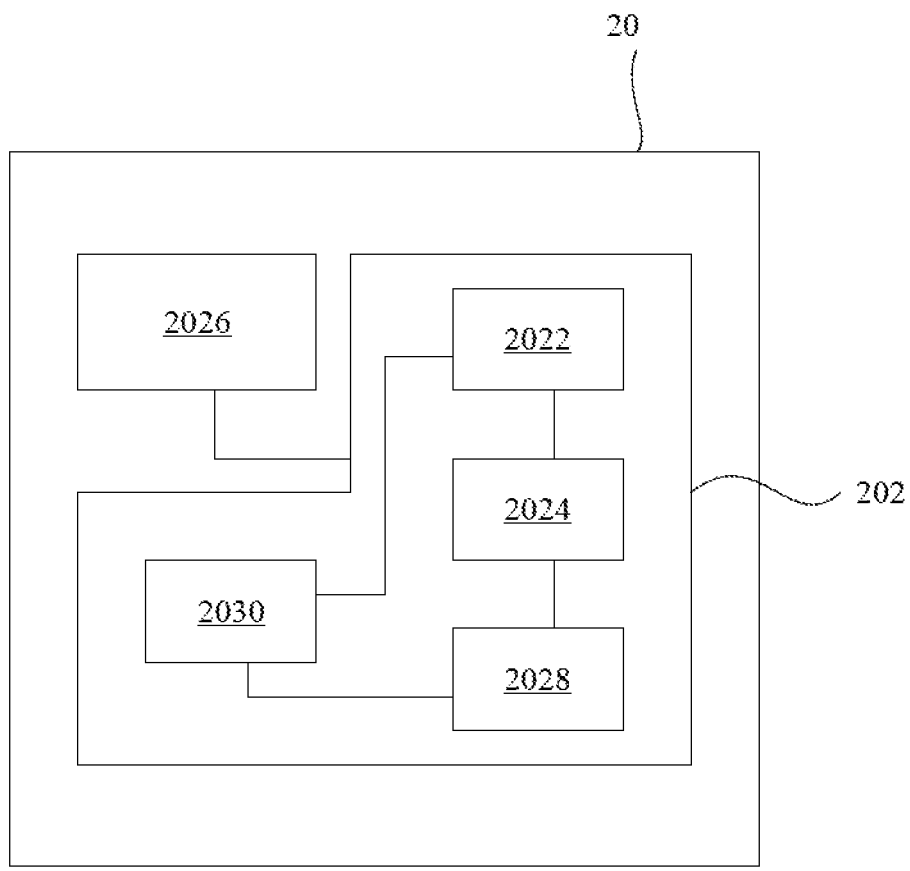
FIG. 3 is a schematic block diagram illustrating a modular main board according to the present invention.

In one embodiment, the metal conductor 40 is attached onto the interior surface of the clothing body 10 through a water-proof and anti-static interference tape. The modular main board 20 and the functional board 30 are fixed onto the clothing body 10 with a fixing component 50. One exemplary fixing component 50 may be, but not restricted to, a water-proof and anti-static interference tape, a Velcro, button or magnetic component FIG. 3 is a schematic block diagram illustrating a modular main board according to the present invention. Please refer to FIG. 3, the modular main board 20 is provided with a first power supply module 2026 and a main functional module 202. The main functional module 202 at least includes a control module 2022, a processing module 2024, a transmission and receiving module 2028 and a memory 2030. The control module 2022, the processing module 2024, the transmission and receiving module 2028 and the memory 2030 may be completely packaged and integrated into a chip or a chipset of single function. Optionally, the modular main board 20 may be selectively provided with two or all of the modules aforementioned for different requirements. Consequently, the modular main board 20 may be customized to meet everybody's requirement.

Furthermore, due to the main functional module 202 of a chip or a chipset of single function, it may be independently developed, up-grated or replaced for removal of damaged functional module. Thus, it is not necessary to drop the whole modular main board 20 just for one or more malfunction functional modules. Accordingly, the modular main board 20 of the present invention reduces pollution on environment and amount of discard electrical components.

Next, the control module 2022 is provided to control the operation of the modular main board 20. The first power supply module 2026, which supplies power to the modular main board 20, may be a battery module or charging-discharging battery module and not restricted to any type or configuration. The transmission and receiving module 2028 is provided to transmit data or signal to the processing module or other electric apparatus (not shown in FIG. 3). The transmission and receiving module 2028 may be, but not limited to, a wireless signal module, a RF signal module or a Bluetooth signal module. The manufacturing of the control module 2022, the processing module 2024, the first power supply module 2026, the transmission and receiving module 2028, and the memory 2030 is well known and not repeated herein. Besides, the main function module 202 is not limited to include the control module 2022, the process-ing module 2024, the first power supply module 2026, the transmission and receiving module 2028, and the memory 2030 aforementioned.

Please refer to FIG. 3 again, the modular main board 20 may include a soft board or a flexible circuit board. By use of the soft board or the flexible circuit board as a substrate of the modular main board 20, the modular main board 20 is adapted to being bent or twisted along with the movement of a body, such as exercising or walking, or the swinging and twisting of the clothing body 10, instead of being dropped to result in damage. Accordingly, by use of the soft board or the flexible circuit board as a substrate of the modular main board 20 improves issues such as good attachment with the clothing body 10, damage on a detection device or a wearable device during the user's putting on or taking off the clothing body 10, or separation from the clothing body 10, when compared to the detection device or the wearable device of a prior design.

Figure 4:
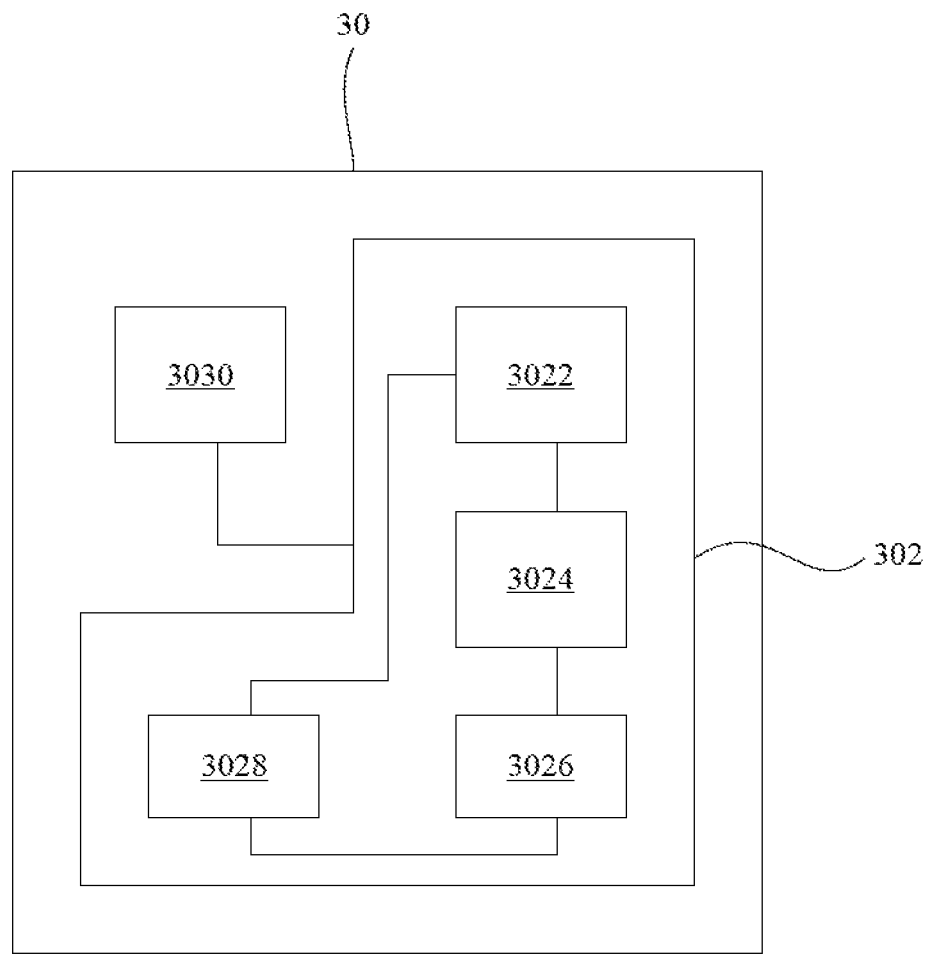
FIG. 4 is a schematic block diagram illustrating a functional board according to the present invention.

Next, FIG. 4 is a schematic block diagram illustrating a functional board of a modular intelligent clothing according to the present invention. Please refer to FIG. 4, the functional board 30 is provided with an auxiliary functional module 302. In one embodiment, the auxiliary functional module 302 may include a sensing module 3022, a transmission and receiving module 3024, a navigating and positioning module 3026 and an alarming module 3028. The electrical connection of these modules on the auxiliary functional module 302, as well as the electrical connection of the auxiliary functional module 302 and the functional board 30, may be implemented by the wires (not shown in the drawing) on the functional board 30. Similarly, to meet different requirements, the functional board 30 may be provided with the sensing module 3022, the transmission and receiving module 3024, the navigating and positioning module 3026, the alarming module 3028 or the combination of two or more modules aforementioned. However, the auxiliary functional module 302 is also not limited to include the sensing module 3022, the transmission and receiving module 3024, the navigating and positioning module 3026, and the alarming module 3028.

Similarly, the auxiliary functional module 302 on the functional board 30 may be a chip or a chipset of single function, as well as the main functional module 202. Thus, similar to the main functional module 202 of a chip or a chipset of single function, the auxiliary functional module 302 may be independently developed, up-grated or replaced for removal of damaged functional module. It is not necessary to drop the whole functional board 30 just for one or more mal-function functional modules. Accordingly, the functional board 30 of the present invention reduces pollution on environment and amount of discard electrical components.

Besides, in one embodiment, the sensing module 3022 is provided to sense physiological signal from human body, such as heart beats, step counts or sleeping, and so on. The navigating and positioning module 3026 detects the location of the user. The transmission and receiving module 3024 is provided to transmit data or signal to the transmission and receiving module 2024 of the modular main board 20 or other electric apparatus. The transmission and receiving module 3024 may be, but not limited to, a wireless signal module, a RF signal module or a Bluetooth signal module. The alarming module 3028 is provided to output an alarm to the transmission and receiving module 2024 of the modular main board 20 for paying the user's or others' attention. The manufacturing of the sensing module 3022, the transmission and receiving module 3024, the navigating and positioning module 3026, and the alarming module 3028 is well known and not repeated herein. Besides, the auxiliary function module 302 is not limited to include the sensing module 3022, the transmission and receiving module 3024, the navigating and positioning module 3026, and the alarming module 3028 aforementioned.

Furthermore, the auxiliary functional module 302 on the functional board 30, which cooperates with the main functional module 202 on the modular main board 20, provides the user with operation of intelligent functions. In one embodiment, there is no power supply module on the functional board 30, and the power for the functional board 30 is supplied by the first power supply module 2026 on the modular main board 20. Practically, due to the modular main board 20 connected to the functional board 30 via the metal conductor 40, the power for the operation of the functional board 30 may be supplied by the first power supply module 2026 on the modular main board 20 via the metal conductor 40. In other embodiment, on condition that the modular main board 20 and the functional board 30 are connected with each other in a way of magnetic induction, the power for the operation of the functional board 30 is supplied by the first power supply module 2026 on the modular main board 20 in the way of magnetic induction. Thus, the weight and volume of the functional board 30 may be reduced because of no power supply module.

Furthermore, the arrangement of both the main functional module 202 on the modular main board 20 and the auxiliary functional module 302 on the functional board 30 may be adjusted for different requirements, which are not restricted to which one is definitely deposited on which.

Figure 5:
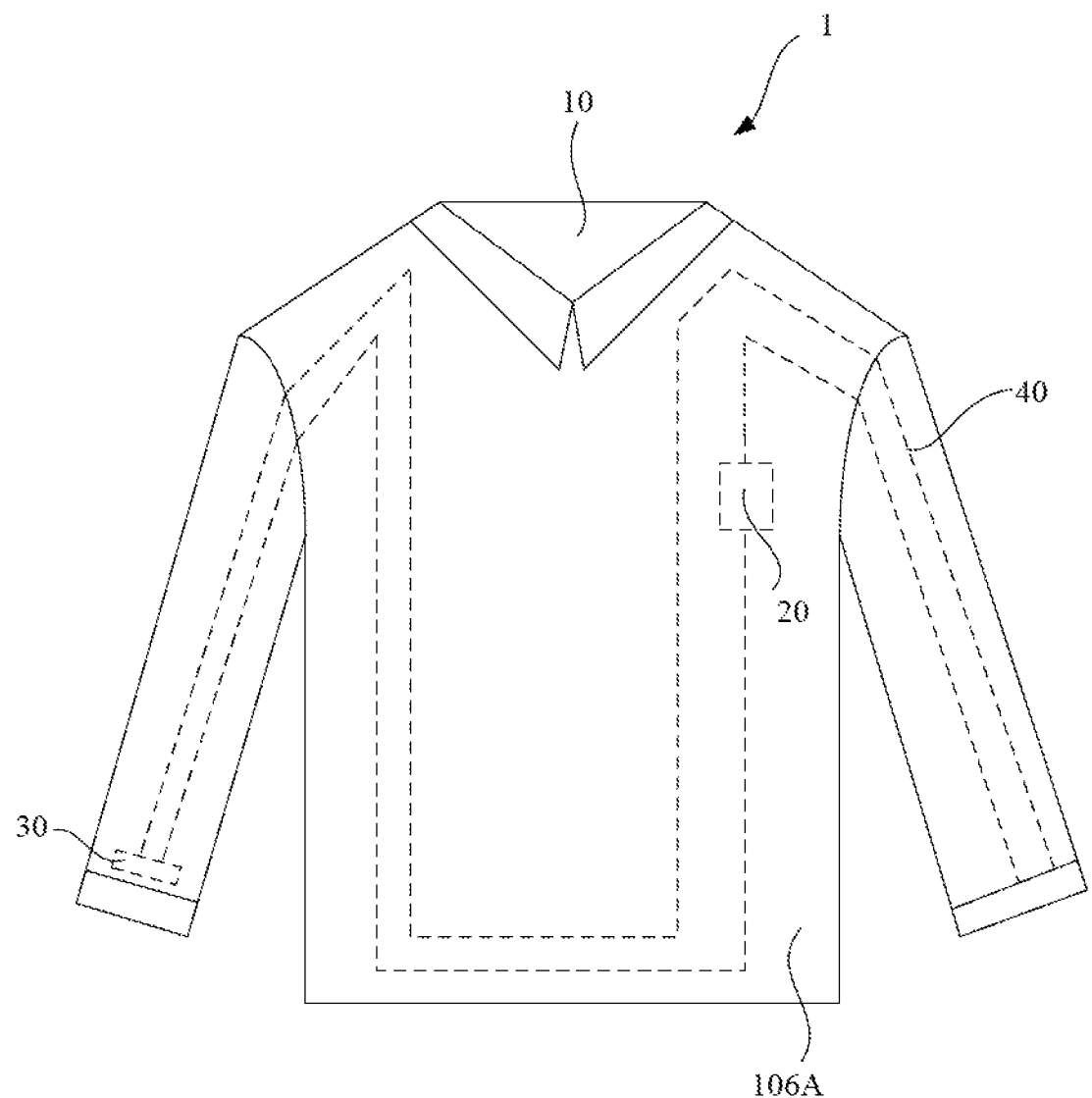
FIG. 5 is a schematic diagram illustrating a modular main board and a functional board respectively arranged within a clothing body according to the present invention.

Accordingly, the combination of the clothing body 10, the modular main board 20 and the functional board 30 is illustrated as following. FIG. 5 is a schematic diagram illustrating the modular main board 20 and the functional board 30 respectively arranged within the clothing body 10 according to the present invention. Please refer to FIG. 5, the clothing body 10 is a coat and the metal conductor 40 is distributed within the clothing body 10 to form a circuit loop, which are similar to the ones aforementioned. The modular main board 20 and the functional board 30 are electrically connected to each other with the metal conductor 40 within the clothing body 10 or in the way of magnetic induction. In the embodiment, the modular main board 20 may be deposited around the chest of the front piece 106A of the clothing body 10, and the functional board 30 may be deposited the left sleeve opening 1022B of the clothing body 10. These arrangements are just exemplary. There is no special restriction to the connection for the clothing body 10. The modular main board 20 and the functional board 30 are deposited on anywhere of the clothing body 10, as long as they have physical connection with the metal conductor 40 or inductive connection in the way of magnetic induction through the metal conductor 40 to achieve a modular intelligent clothing 1 for the clothing body 10. It is noted that magnetic induction is implemented by arranging coils within the modular main board 20 and the functional board 30, respectively. Current passes on condition of the modular main board 20 connecting the power to generate magnetic energy and further generate electromagnetic induction. The coils within the functional board 30 induces in response to electromagnetic signal from the modular main board 20 and then generates electric power through changes of magnetic field to supply power to the functional board 30. In the embodiment, the modular main board 20 is provided with the control module 2022, the processing module 2024, the first power supply module 2026, the transmission and receiving module 2028 and the memory 2030, shown as FIG. 3. The functional board 30 is provided with the sensing module 3022, a transmission and receiving module 3024 and the alarming module 3028, shown as FIG. 4. Furthermore, the power of the functional board 30 is supplied by the first power supply module 2026 of the modular main board 20.

Accordingly, when the user wears the clothes with the modular main board 20 and the functional board 30, the current physiological signals, such as heart beats or step counts, may be sensed by the sensing module 3022 of the functional board 30, transferred by the transmission and receiving module 3024 to the transmission and receiving module 2028 of the modular main board 20, and processed by the processing module 2024. The control module 2022 transfers the processed physiological signals with the transmission and receiving module 2028 to other apparatus via a wireless module, RF module, or Bluetooth module. The other apparatus, such as a smartphone or a smart tablet may acquire the user's physiological state with the processed physiological signals.

With a trend of aging society, elder people are vulnerable to losing directions or getting lost. One of issues for elder people wearing a wearable apparatus is to fail in detecting elder people because the wearable apparatus is possibly took off by elder people. The modular intelligent clothing 1 of the present invention is both friendly for elder people without in-monitor feeling and necessary for elder people to wear it once they cover their bodies with it. For user's requirement, the functional board 30 is provided with the navigating and positioning module 3026. The navigating and positioning module 3026 detects the location of the user wearing the modular intelligent clothing 1 and transfers position signal to the transmission and receiving module 2028 of the modular main board 20. After the processing module 2024 processes the position signal, the control module 2022 transfers the processed position signal to the family of the elder user via the transmission and receiving module 2028. Consequently, the family of the elder user may find the location of the elder user via such a positioning way when the elder user goes outside, so that possibilities of losing direction or getting lost for elder people can be reduced, as well as danger generation. Besides, in other embodiment, the clothing body 10 may be equipped with the modular main board 20 without the functional board 30, for different requirement.

Next, a pairing system for the modular intelligent clothing is illustrated herein. One exemplary pairing system includes the clothing body 10 itself, the modular main board 20, and the functional board 30. The clothing body 10, the modular main board 20 and the functional board 30 are identical to the ones aforementioned and not repeated herein. It is noted that the modular main board 20 and the functional board 30 are deposited at any position within the clothing body 10, respectively. In one embodiment, there is a circuit loop within the clothing body 10, such as the metal conductor 40 aforementioned. In case that the functional board 30 electrically connects to the metal conductor 40 and locates on the circuit loop, the transmission and receiving module 2028 on the modular main board 20 is triggered by the on-state circuit to if an apparatus to match. The matching with the apparatus may be completed once the apparatus is found and confirmed by the user, and be cooperated with the modular main board 20 to supply power to the functional board 30 or operate.

In other embodiment, in case that the modular main board 20 and the functional board 30 are deposited within the range of magnetic induction via the metal conductor 40 around the modular main board 20 and electrically connected with each other in the way of magnetic induction, the transmission and receiving module 2028 on the modular main board 20 within the clothing body 10 is triggered if an apparatus within the range of magnetic induction to match. In such a situation the transmission and receiving module 3024 of the functional board 30 is enabled to work. The matching with the apparatus may be completed once the apparatus is found and confirmed by the user, and be cooperated with the modular main board 20 to supply power in the way of magnetic induction to the functional board 30 or operate.

Figure 6:
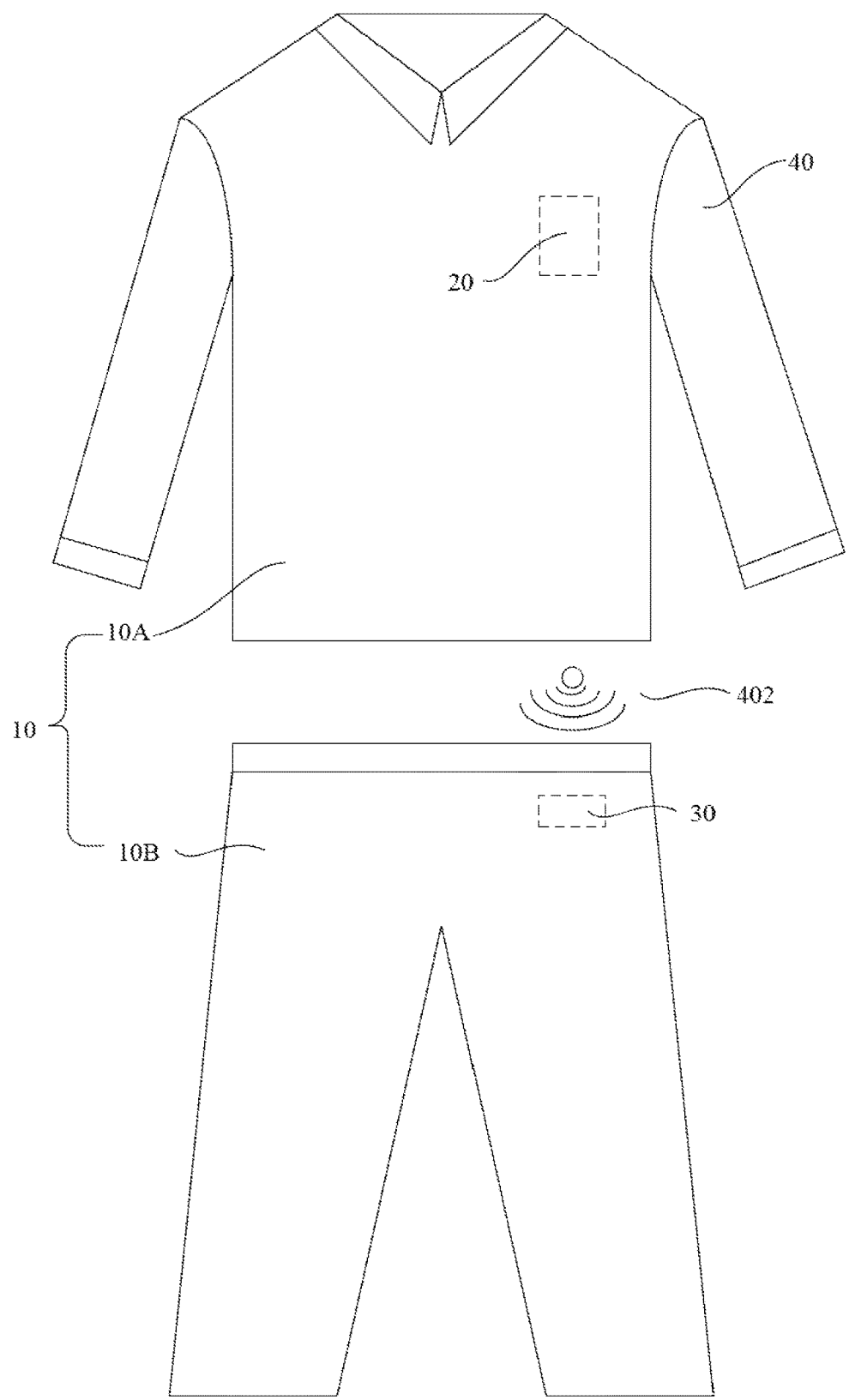
FIG. 6 is a schematic diagram illustrating a modular main board and a functional board arranged within a clothing body according to the present invention.

FIG. 6 is a schematic diagram illustrating a modular main board and a functional board arranged within a clothing body according to the present invention. Please refer to FIG. 6, the clothing body 10 including a coat 10A and pants 10B does not have any metal conductor. In this embodiment, similar to the one of FIG. 3, the modular main board 20 is provided with the control module 2022, the processing module 2024, the first power supply module 2026, the transmission and receiving module 2028 and the memory 2030. Besides, similar to the one of FIG. 4, the functional board 30 is provided with the sensing module 3022, the transmission and receiving module 3024, the navigating and positioning module 3026 and the alarming module 3028, and further provided with a second power supply module 3030. In this embodiment, the modular main board 20 and the functional board 30 communicate with each other in a wireless way. Without physical wires layout and power supply, the modular main board 20 may be deposited at the coat 10A of the clothing body 10 and the functional board 30 may be deposited at any position of the pants 10B of the clothing body 10 such as a leg or waist. Accordingly, physiological signal sensed by the sensing 3022 on the functional board 30 is transferred by the transmission and receiving module 3024 on the functional board 30 to the transmission and receiving module 2028 on the modular main board 20. Positioning signal may be transferred by the navigating and positioning module 3026 on the functional board 30 through the transmission and receiving module 3024 to the transmission and receiving module 2028 on the modular main board 20 in a wireless way, such as WiFi, Bluetooth, or ZigBee.

In this embodiment, in case that the modular main board 20 and the functional board 30 are electrically connected with each other in the wireless way, for example, the functional board 30 deposited within a range of wireless transmission of the modular main board 20, the transmission and receiving module 2028 on the modular main board 20 within the clothing body 10 starts to if an apparatus within the range of wireless transmission to match. In such a situation the transmission and receiving module 3024 of the functional board 30 is enabled to work. The matching is completed once the apparatus is found and confirmed by the user, and be cooperated with the modular main board 20 to supply power in the wireless way to the functional board 30 or operate.

Accordingly, the modular intelligent clothing 1 of the present invention improves convenience of current intelligent life. The modular main board 20 and the functional board 30 can be customized according to user's requirement so as to improve convenience for user. Besides, both modular main board 20 and the functional board 30 of the soft boards within the clothing body 10 are comfortable to user during putting on, wearing or taking off it, as well as good fixing and long lifetime. Furthermore, the modular main board 20 may be viewed as a hub to set or control the functional board 30, or be as a middle station for an intelligent terminal such as a smartphone or a tablet, which is convenient for user to control, set, or operation.

What is claimed is:

1. A modular intelligent clothing, comprising:
   a clothing body;
   a metal conductor, the metal conductor is arranged in the clothing body to form a circuit loops therein;
   a modular main board, the modular main board is disposed at any position of the clothing body, electrically connected with the metal conductor, and having a power supply module therein; and
   a functional board, the functional board is disposed at any position of the clothing body and electrically connected with the modular main board,
   wherein the modular main board is electrically connected with the functional board by a magnetic induction, and the modular main board supplies a power supply module for the functional board through the magnetic induction.

2. The modular intelligent clothing according to claim 1, wherein the metal conductor is constituted by a metal wire or a plurality of metal wires.

3. The modular intelligent clothing according to claim 1, wherein the metal conductor is distributed in a spiral in the clothing body.

4. The modular intelligent clothing according to any one of claim 1, wherein the metal conductor is a soft metal wire.

5. The modular intelligent clothing according to claim 1, wherein the modular main board is electrically connected with the functional board by the metal conductor.

6. The modular intelligent clothing according to claim 1, wherein the modular main board having a main functional module, and the main functional module at least includes a control module, a processing module, a transmission and receiving module, a memory, or any combination of above.

7. A pairing system is used for the modular intelligent clothing, comprising:
   a clothing body;
   a modular main board, the modular main board is disposed at any position of the clothing body; and
   a functional board, the functional board is disposed at any position of the clothing body, and the functional board is electrically connected with the modular main board, wherein a power supply module is configured to supply a power to the modular main board or the functional board,
   wherein the pairing system further comprising a metal conductor is arranged in the clothing body to form a circuit loops therein, and when the functional board is disposed on the circuit loops, the modular main board is triggered to be matched with the functional board.

8. The pairing system according to claim 7, wherein when the functional board is disposed within a magnetic induction range of the modular main board, the modular main board is triggered to be matched with the functional board through a magnetic induction.

9. The pairing system according to claim 7, wherein the modular main board is a hub for modular setting or controlling the functional board.

10. The pairing system according to claim 7, wherein the modular main board is used as a hub through other intelligent terminals.

* * * * *